US010238879B2

(12) United States Patent
Bobgan et al.

(10) Patent No.: US 10,238,879 B2
(45) Date of Patent: Mar. 26, 2019

(54) IMPLANTABLE MEDICAL DEVICES WITH FLEXIBLE INTERCONNECT HAVING STRAIN RELIEF

(71) Applicant: CARDIAC PACEMAKERS, INC, St. Paul, MN (US)

(72) Inventors: Jean M. Bobgan, Maple Grove, MN (US); Moira B. Sweeney, St. Paul, MN (US); James E. Blood, Shoreview, MN (US); Robert A. Jones, Lake Elmo, MN (US); John E. Hansen, Ham Lake, MN (US); Keith R. Maile, New Brighton, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 122 days.

(21) Appl. No.: 15/058,302

(22) Filed: Mar. 2, 2016

(65) Prior Publication Data

US 2016/0287880 A1    Oct. 6, 2016

Related U.S. Application Data

(60) Provisional application No. 62/143,388, filed on Apr. 6, 2015.

(51) Int. Cl.
*A61N 1/375* (2006.01)
*A61N 1/39* (2006.01)
*A61N 1/37* (2006.01)

(52) U.S. Cl.
CPC .......... *A61N 1/375* (2013.01); *A61N 1/3968* (2013.01); *A61N 1/3718* (2013.01); *A61N 1/3931* (2013.01); *A61N 1/3956* (2013.01)

(58) Field of Classification Search
CPC .... A61N 1/375; A61N 1/3752; A61N 1/3718; A61N 1/331; A61N 1/3968; H05K 1/1147; H05K 1/189; H05K 1/3956
USPC ........................................................ 607/116
See application file for complete search history.

(56) References Cited

U.S. PATENT DOCUMENTS

| 5,144,946 | A | 9/1992 | Weinberg et al. |
| 6,445,948 | B1 | 9/2002 | Somdahl et al. |
| 7,020,525 | B1 | 3/2006 | Davis et al. |
| 7,187,974 | B2 | 3/2007 | Haeg et al. |
| 7,544,220 | B2 | 6/2009 | Zhao et al. |
| 7,769,457 | B2 | 8/2010 | Fonte |
| 8,473,056 | B2 | 6/2013 | Engmark et al. |

(Continued)

OTHER PUBLICATIONS

"Flexible Circuit Design Guide, Fourth Edition", Teledyne Electronic Technologies, pp. 1-81.

*Primary Examiner* — Michael Kahelin
*Assistant Examiner* — Minh Duc Pham
(74) *Attorney, Agent, or Firm* — Seager, Tufte & Wickhem LLP

(57) ABSTRACT

Implantable medical devices including interconnections having strain-relief structure. The interconnections can take the form of flexible circuits. Strain relief gaps and shapes are integrated in the interconnections to relieve forces in each of three dimensions. In some examples, the region of an interconnection which couples with a component of the implantable medical device is separated by a strain relief gap from a connection to a second component and/or a location where the flex bends around a corner.

15 Claims, 20 Drawing Sheets

(56) References Cited

U.S. PATENT DOCUMENTS

| | | | |
|---|---|---|---|
| 2011/0121922 A1* | 5/2011 | Blair | H01P 3/00 333/238 |
| 2011/0257711 A1* | 10/2011 | Lindner | A61N 1/3752 607/72 |
| 2012/0069536 A1 | 3/2012 | Sporon-Fiedler et al. | |
| 2013/0324862 A1 | 12/2013 | Kalgren et al. | |
| 2014/0214143 A1* | 7/2014 | Levy | A61N 1/375 607/116 |

* cited by examiner

IMPLANTABLE MEDICAL DEVICES WITH FLEXIBLE INTERCONNECT HAVING STRAIN RELIEF

CROSS REFERENCE TO RELATED APPLICATIONS

The present application claims the benefit of and priority to U.S. Provisional Patent Application Ser. No. 62/143,388, filed on Apr. 6, 2015, the disclosure of which is incorporated herein by reference.

BACKGROUND

Implantable medical devices serve a variety of therapeutic and diagnostic purposes. Many such devices include electronic circuits, power supplies and other components. For reasons of economy, reliability and size, devices are often made with modular designs having separate components for different functions, which must be electrically coupled together. New and alternative designs for interconnecting the components of devices are desired.

OVERVIEW

The present inventors have recognized, among other things, that a problem to be solved is that, with close fitting modular electronic designs used in implantable medical devices, the interconnects between modules are sometimes sources of difficulties with reliability and/or manufacturability. With static or cyclic loading, stress/strain on electrical connectors and associated connections to individual components can impact reliability.

A first non-limiting example takes the form of an implantable medical device (IMD) comprising a first component having a connection area, a connector for coupling to the first component and having a first region and a second region for coupling to connection area of the first component, the connector comprising a flex circuit in at least the second region, wherein the second region of the connector comprises a strain relief section to provide strain relief relative to the connection area.

A second non-limiting example takes the form of an IMD as in the first non-limiting example, wherein the connection area of the first component lies in a first plane, and the first region of the connector lies in a second plane different from the first plane. A third non-limiting example takes the form of an IMD as in either of the first two non-limiting examples, wherein the connector extends from the first region to the first region around a bending location. A fourth non-limiting example takes the form of an IMD as in any of the first three non-limiting examples, wherein the first plane defines X and Y dimensions in the first plane and a Z direction orthogonal to the first plane, with the X direction being parallel to a bend defined at the bending location, and the strain relief provides strain relief relative to motion in at least one of the X, Y and Z directions. A fifth non-limiting example is an IMD as in the fourth non-limiting example, wherein the strain relief section comprises a C-shaped portion having an arc around a gap, the gap having a depth and a width, the depth being greater than the width and extending in the X direction.

A sixth non-limiting example takes the form of an IMD as in any of the first to fifth non-limiting examples, wherein the connection area of the first component includes one or more pins, and the connector first region comprises one or more through holes for connection to the one or more pins. A seventh non-limiting example takes the form of an IMD as in the sixth non-limiting example, wherein the strain relief section includes a gap that partly encircles at least one of the through holes.

An eighth non-limiting example takes the form of an IMD as in any of the first to seventh non-limiting examples, wherein the connector is coupled to a second component in the second region, and the second region also includes a strain relief section. A ninth non-limiting example takes the form of an IMD as in any of the first to eighth non-limiting examples, wherein the connector comprises at least one trace for coupling to the first component which includes an impedance matching microstrip. A tenth non-limiting example takes the form of an IMD as in any of the first to eighth non-limiting examples wherein the connector comprises at least one trace for coupling to the first component which includes a coplanar waveguide.

An eleventh non-limiting example takes the form of an IMD as in any of the first to tenth non-limiting examples wherein the first component is selected from the group consisting of a battery, a capacitor, or a hybrid carrying circuitry. A twelfth non-limiting example takes the form of an IMD as in any of the first to eleventh non-limiting examples wherein the connector is manufactured by the use of laser cutting to create the strain relief. A thirteenth non-limiting example takes the form of an IMD as in any of the first to twelfth non-limiting examples wherein the connector is one of a two-layer or a three layer flex circuit.

A fourteenth non-limiting example takes the form of an implantable medical device (IMD) comprising a first component having a first connection area; a second component having a second connection area; a connector for coupling to each of the first and second connection areas and including an S-curve between the first and second connection areas to provide strain relief therebetween. A fifteenth non-limiting example takes the form of an IMD as in the fourteenth non-limiting example wherein the first connection area lies on a first plane, and the second connection area lies in a second plane at an angle of at least 45 degrees relative to the first plane. A sixteenth non-limiting example takes the form of an IMD as in either of the fourteenth and fifteenth non-limiting examples, wherein the first component is a header having an antenna, and the second component is a hybrid having operational circuitry including signal transmission circuitry for providing a signal to the antenna for transmission, wherein the connector includes an S-curve comprising transmission line elements to provide an impedance matched connection between the antenna and the signal transmission circuitry.

A seventeenth non-limiting example takes the form of a method of assembling an implantable medical device (IMD) having a plurality of modular elements each having a respective connection area, the method comprising attaching an interconnector device to a first modular element, attaching the interconnector device to a second modular element, and bending the interconnector device, wherein the interconnector device is a flex circuit having a first region for connecting to the first modular element and a second region for connecting to the second modular element, further wherein the interconnector device comprises at least one strain relief section to provide strain relief in at least one of the first region and the second region, and finally wherein the step of bending the interconnector device includes imparting a bend in the flex circuit between the first and second regions.

An eighteenth non-limiting example takes the form of a method as in the seventeenth non-limiting example, wherein the first region of the interconnector device comprises one or more through-holes for connection to pins of the first modular element, and the step of attaching the interconnector device to the first modular element comprises soldering the one or more through holes of the first region to the pins of the first modular element, and wherein the bending step occurs about an axis and the strain relief structure is configured to relieve strain in the direction of the axis (X) as well as each of two orthogonal directions (Y, Z) relative to the axis, wherein X, Y and Z are all mutually orthogonal. A nineteenth non-limiting example takes the form of a method as in the seventeenth non-limiting example, wherein the step of bending occurs about an axis and at least a portion of the first region adjacent the axis extends parallel to the axis, with the strain relief providing a gap between the area the bending occurs and the location where the first region of the interconnector is connected to the first modular element.

A twentieth non-limiting example takes the form of a method as in any of the seventeenth to nineteenth non-limiting examples, wherein the strain relief structure comprises a gap surrounded by a generally C-shaped portion that enables the first region to absorb motion in several dimensions.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
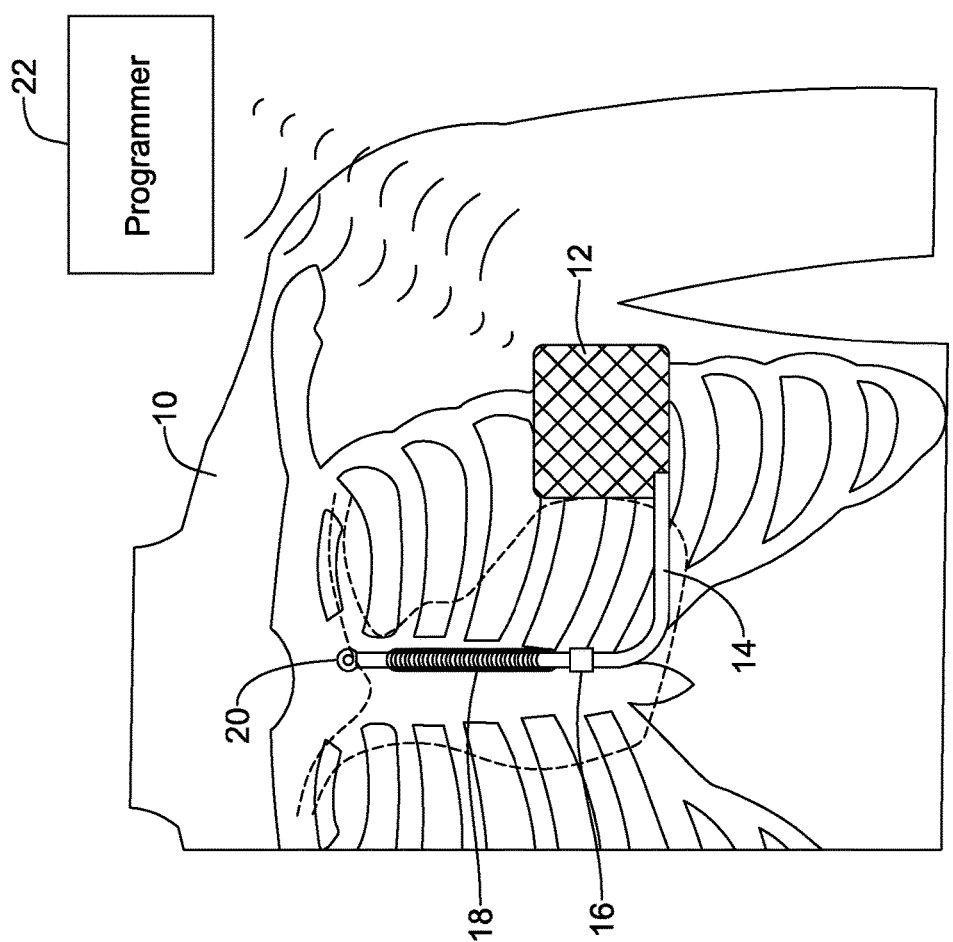
FIG. 1 shows an illustrative implantable medical device system implanted in a patient.

FIG. 1 shows an illustrative implantable medical device system implanted in a patient. This particular example shows a subcutaneous cardiac device system implanted in a patient 10, over the patient's ribs and beneath the skin. A canister 12 is implanted, in the example, at approximately the left axilla (armpit), beneath the arm. A lead 14 extends from the canister 12 toward the patient's xiphoid and then over or slightly to the left of the sternum and toward the manubrium. The lead 14 includes electrodes 16, 18 and 20, with electrode 18 illustrated as a coil electrode designed primarily for shock delivery (though sensing via coil electrode 18 may be performed as well). The other electrodes 16 and 20 on lead 14 are shown as ring and cap electrodes, respectively. Other designs may be used. The canister 12, in this example, includes a conductive surface or, if desired, has an area on its surface which is conductive to allow for at least sensing of electrical signals and, when needed, therapy delivery.

A programmer 22 is provided for communicating with and controlling operation of the implanted system, as is well known in the art. Such communication can be useful to configure the implanted system for sensing, therapy or other feature, to load new software or firmware for the implanted system, and to retrieve information about system operation such as device status, therapy history, diagnostic information (device and/or patient related), or other suitable data.

The medical device system of FIG. 1 is merely one illustration. Other configurations and implant locations may be used instead. Cardiac devices may be implanted in other subcutaneous locations, and/or may be transvenous systems, epicardial systems, intravascular systems and may include therapy delivery systems or monitoring devices. The lead 14 may be differently placed, for example extending into the vasculature of the patient and to the heart, wrapping around the patient's torso to the back, or passing beneath/behind the sternum. Other active implantable devices include drug or insulin pumps, proposed artificial pancreas devices, and neurostimulation or neuromodulation systems which can be used in numerous ways such as pain treatment, seizure prevention, treatment of progressive diseases such as Parkinson's or Alzheimer's disease, therapy for digestive or breathing or other disorders, either in use already or undergoing research and development.

Figure 2:
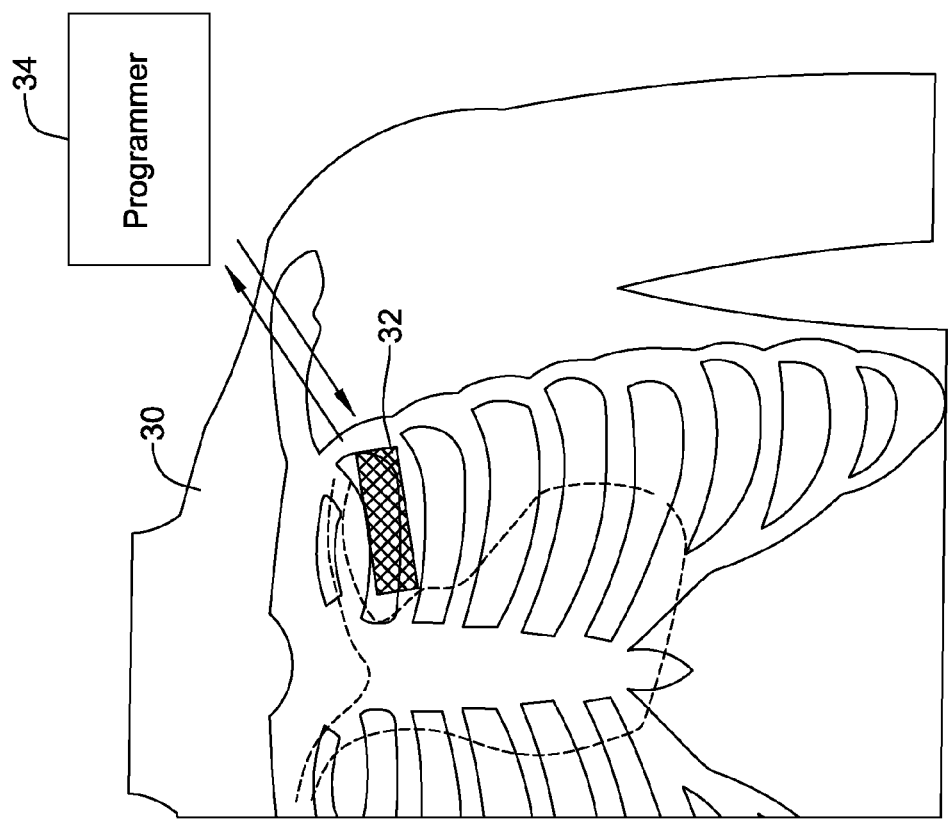
FIG. 2 shows an illustrative cardiac monitoring device.

FIG. 2 shows an illustrative cardiac monitoring device. A patient 30 can receive the device 32 in the upper left quadrant, though other locations may be used. Implantation is performed to monitor the cardiac rhythms of the patient, often with a goal of determining whether an active implant such as a pacemaker or defibrillator may benefit the patient, or whether a surgical or pharmaceutical intervention is advisable. For example, unexplained episodes of syncope may be diagnosed using an implantable monitor 32, and determinations of atrial fibrillation burden may also be had.

The monitor 32 will have a plurality of electrodes on one or more outer surfaces to enable it to capture cardiac electrical signals. Communications circuitry will be provided for communicating to a programmer 34 to allow downloading of patient cardiac data and observation of device status.

The canister 12 (FIG. 1) or canister 32 (FIG. 2) contain operational circuitry for controlling the operation of the device including, for example, various logic circuits, amplifiers, filters, and, often, a microcontroller or microprocessor. Communication circuitry may be provided for use in one or more of inductive, RF or conducted communication. This operational circuitry may be provided on a one or more "hybrids", usually a circuit board (often a flexible circuit or rigid-flex circuit) having the relevant application specific integrated circuitry, processors and logic. More than one hybrid may be used, for example, a high power and low power hybrid may be included, with coupling therebetween, to avoid high power functions interfering with low power functions. These devices will include batteries and, for those with high power therapy outputs, high power capacitors, or other separate circuitry such as an actuator for controlling the output of therapeutic substances, for example. Often a separate header is provided for allowing hermetically sealed connection to one or more leads or electrodes.

Modular design is often used to facilitate manufacturing processes. For example, a device may have a hybrid having operational circuitry thereon, a battery, a high power capacitor, and a header, each being coupled to one another within the device using flexible connectors, with one or more of these components added sequentially during various stages of manufacturing. For example, staged manufacturing may begin with the hybrid(s) having operational circuitry, which are verified to function and/or calibrated at one manufacturing stage. In a subsequent manufacturing stage, the high power capacitors are connected to the hybrid(s), and functionality is again verified. Then the batteries may be connected, with functionally retested. The entire assembly can then be placed in the device canister (if not already there) and/or attached to the header, and functionality is retested. Hermetic sealing next takes place, with final testing performed after hermetic sealing and/or sterilization. This method overview is not intended to be limiting, but is merely exemplary.

The flexible interconnections can be source of electrical failure, and so manufacturers go to significant lengths to achieve highly reliable interconnections. For example, during design validation testing, implantable devices are subjected to static and cyclic loading (such as vibration, drop, and compression tests). During such tests, the individual, modular components in the device subject the interconnections to various strains and stresses.

Figure 3:
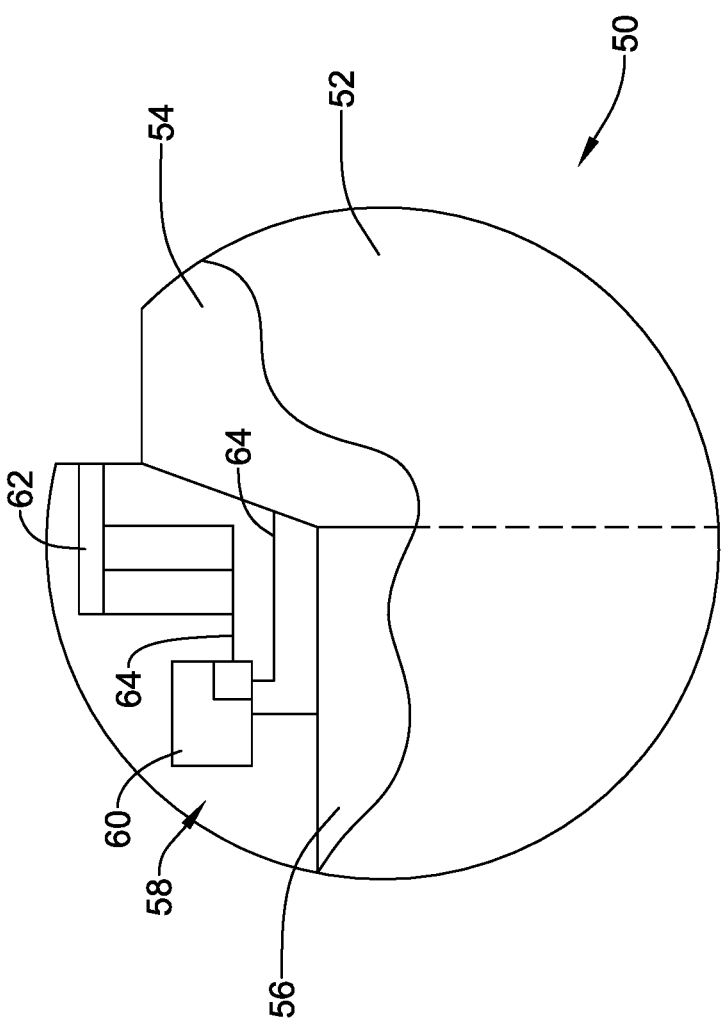
FIG. 3 shows a partial cut-away view of an implantable device housing operational circuitry and components.

FIG. 3 shows a partial cut-away view of an implantable device housing operational circuitry and components. The device 50 may include an outer hermetic housing 52, which is often formed of metal but could use other materials. Inside the housing 52 are a capacitor 54 and battery 56, each coupled to a hybrid 58 having operational circuitry 60 thereon. A header 62 is provided and couples to the operational circuitry 60 as well. Several interconnects 64 couple the operational circuitry 60 to the header 62 and other components 54, 56.

Figure 4:
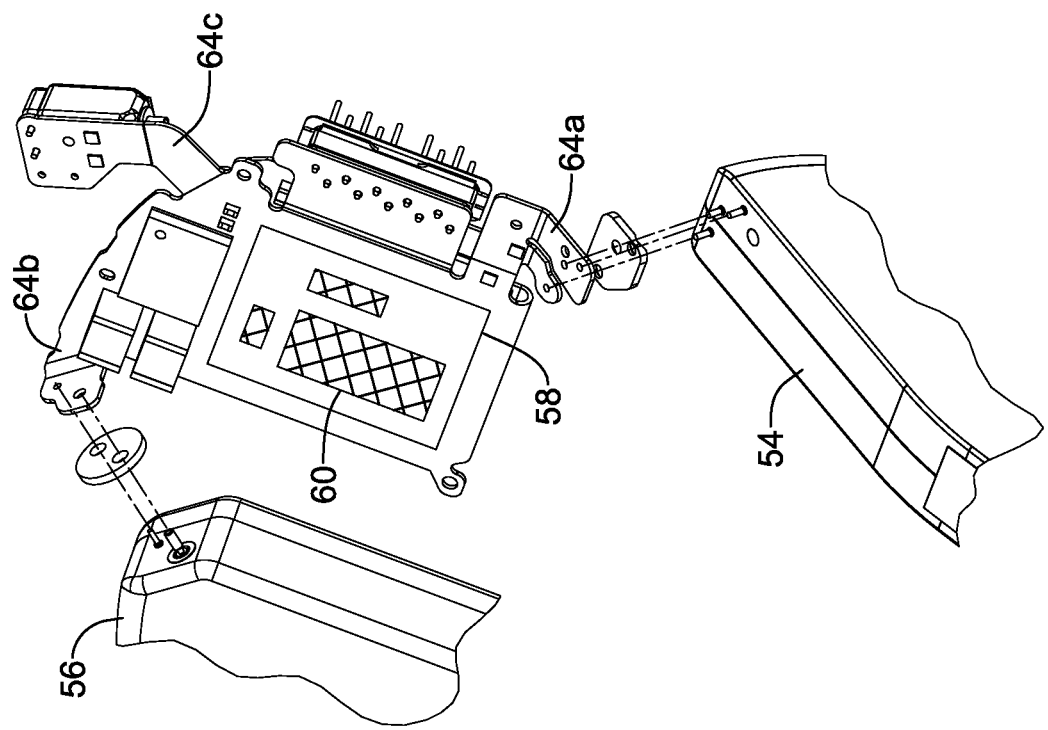
FIG. 4 is an exploded view of an implantable device showing interconnection of operational circuitry and components.

FIG. 4 is an exploded view of an implantable device showing interconnection of operational circuitry and components. The capacitor 54 is connected to the hybrid 58 with a flexible tab 64A, which is essentially an extension of the flex circuit on which the operational circuitry 60 of the hybrid 58 resides. A flexible tab 64B couples to the battery 56, and yet another flexible tab 64C has a set of feedthrough pins for coupling to the header (not shown). As can be seen, the connections require manipulation each of three different dimensions. During manufacturing, each flex tab 64A, 64B, 64C undergoes bending and soldering to secure the relevant component it attaches to.

Figure 5A:
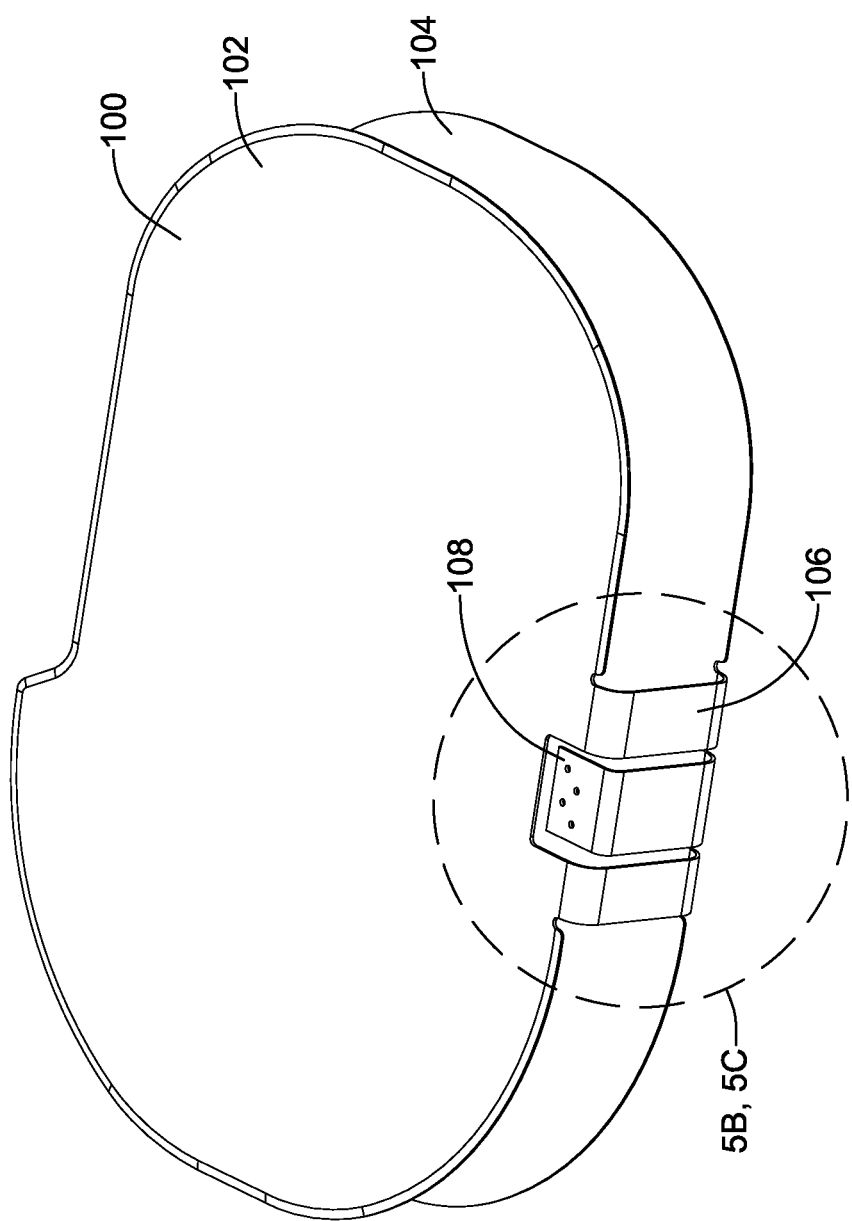
FIGS. 5A-5C illustrate a device shield component and highlight certain difficulties with attachment thereto.
Figure 5B:
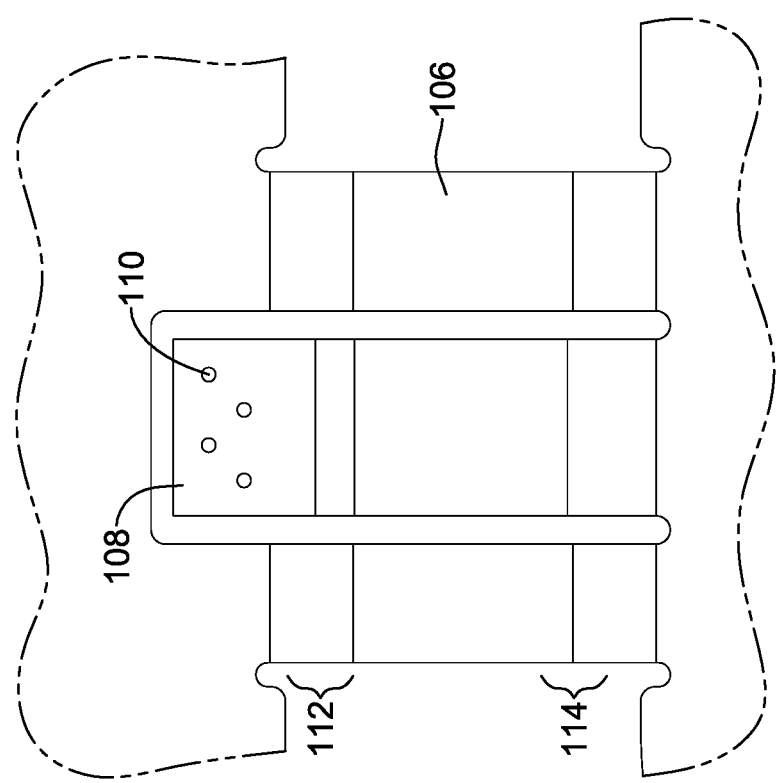
Figure 5C:
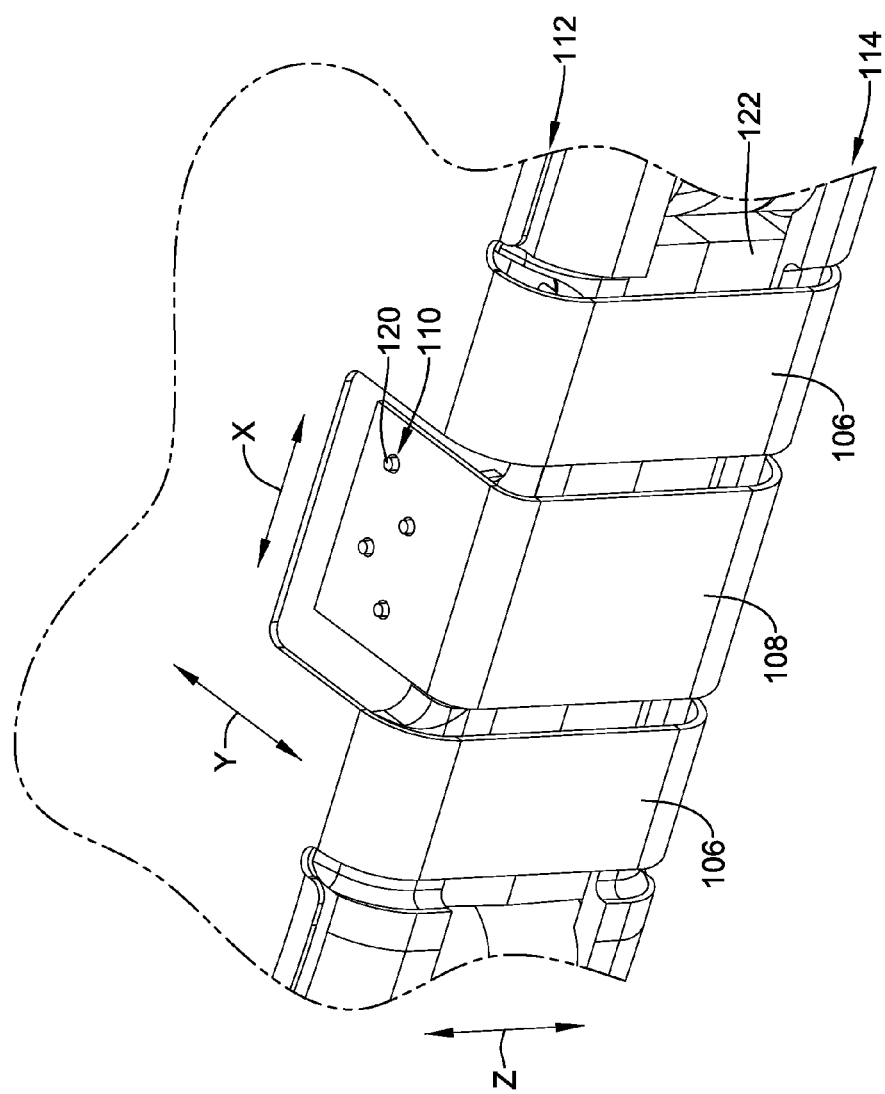

FIGS. 5A-5C illustrate a device shield component and highlight certain difficulties with attachment thereto. Referring to FIG. 5A, in this example, a device shield 100 is illustrated including two leafs 102, 104, coupled together at junction arms 106, adjacent to a connector 108 for connecting to operational circuitry. The shield 100 may take the form of a number of layers of conductors or dielectric, as the case may be. Illustrative shields are shown, for example, in U.S. Pat. Nos. 7,769,457 and 5,814,090, and U.S. Provisional Pat. App. No. 62/143,463, titled IMPLANTABLE MEDICAL DEVICES HAVING FLEXIBLE ELECTROMAGNETIC INTERFERENCE AND DUMP RESISTOR SHIELDS, the disclosure of which is incorporated herein by reference.

The shield 100 may be provided to electrically insulate operational circuitry and other components. For example, some implantable devices use all or a portion of the canister housing the circuitry and components to deliver electrical therapy, meaning that the canister of the device is not at ground for the system during therapy. The shield 100 may prevent the non-grounded canister from coming into contact with the operational circuitry or other components and interfering with operation. In some examples, shield 100 may also be useful to prevent arcing or corona discharge between an active canister and the operational circuitry and components during high power electrical outputs, as noted in U.S. Pat. No. 7,769,457 and U.S. Provisional Pat. App. No. 62/143,463, titled IMPLANTABLE MEDICAL DEVICES HAVING FLEXIBLE ELECTROMAGNETIC INTERFERENCE AND DUMP RESISTOR SHIELDS, the disclosure of which is incorporated herein by reference.

Referring to FIG. 5B, the area of the junction arms 106 and connector 108 is highlighted. The connector 108 extends to a number of small through-holes 110 where pins from the circuit board of the operational circuitry can be inserted and soldered to the shield 100. Each of the junction arms 106 and the connector 108 have to bend at first location 112 and second location 114 to wrap around the operational circuitry and components of the implantable medical device, as shown in FIG. 5C.

In FIG. 5C, the junction arms 106 and connector 108 wrap around the other components and circuitry of the device, as shown at 122. The connector 108 is attached by soldering the pins 120 of the circuitry 122 at the through holes 110. This structure requires careful planning and spacing, and close tolerances. The design does not provide for strain relief relative to the pins 120 and through holes 110. Movement in each of the X and Y directions due to vibration or impact strains and stresses the 120 pins and through holes 110. Shifting in the Z direction, as may occur under a rib compression test, for example, will tend to push the through holes 110 up and down relative to the pins 120, placing strain on the pins 120 and underlying circuit board, as well as at bend 112.

Figure 6A:
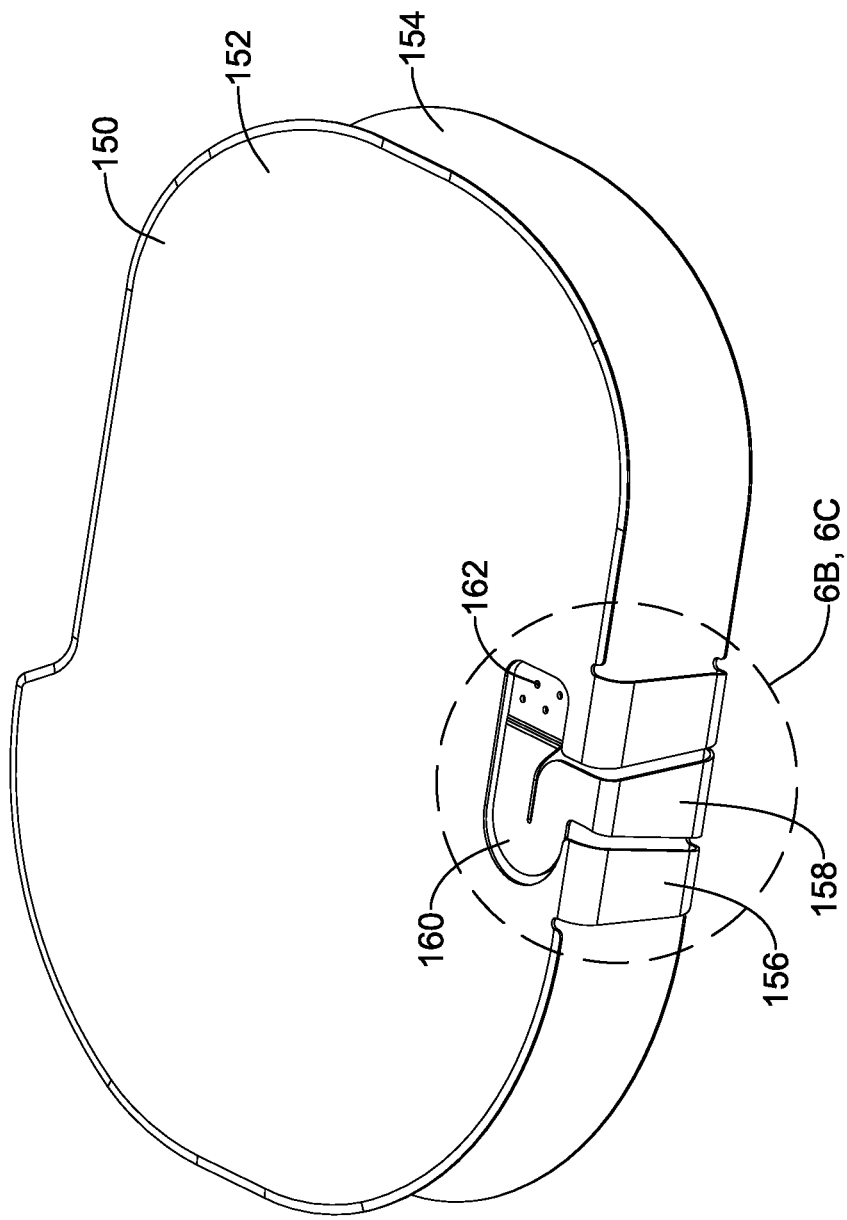
FIGS. 6A-6C show a first illustrative embodiment improving upon the example of FIGS. 5A-5C.
Figure 6B:
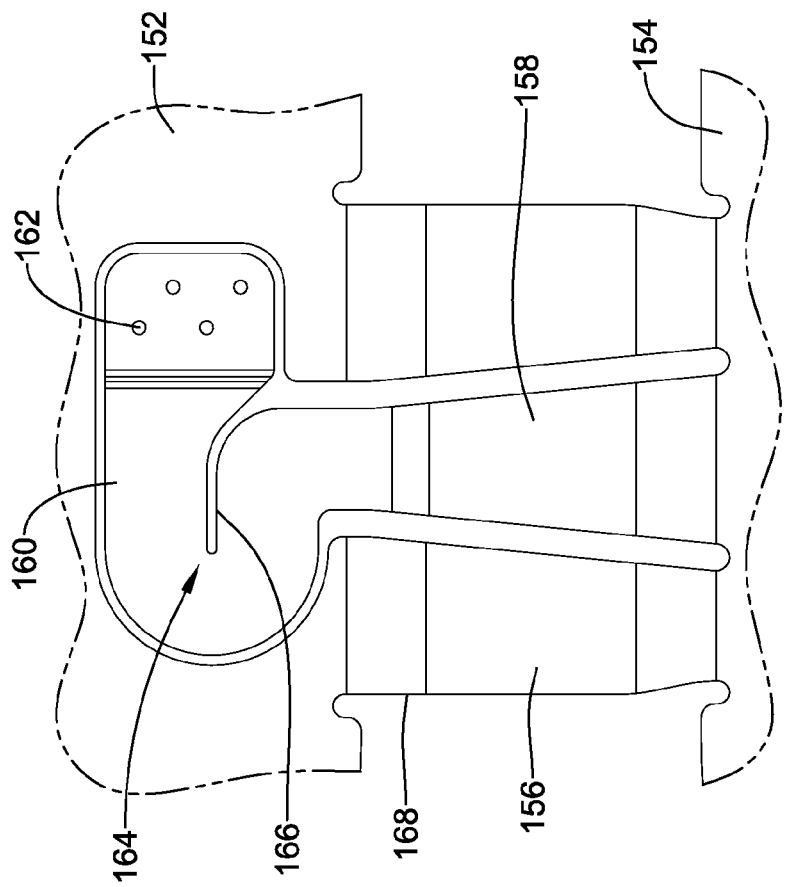
Figure 6C:
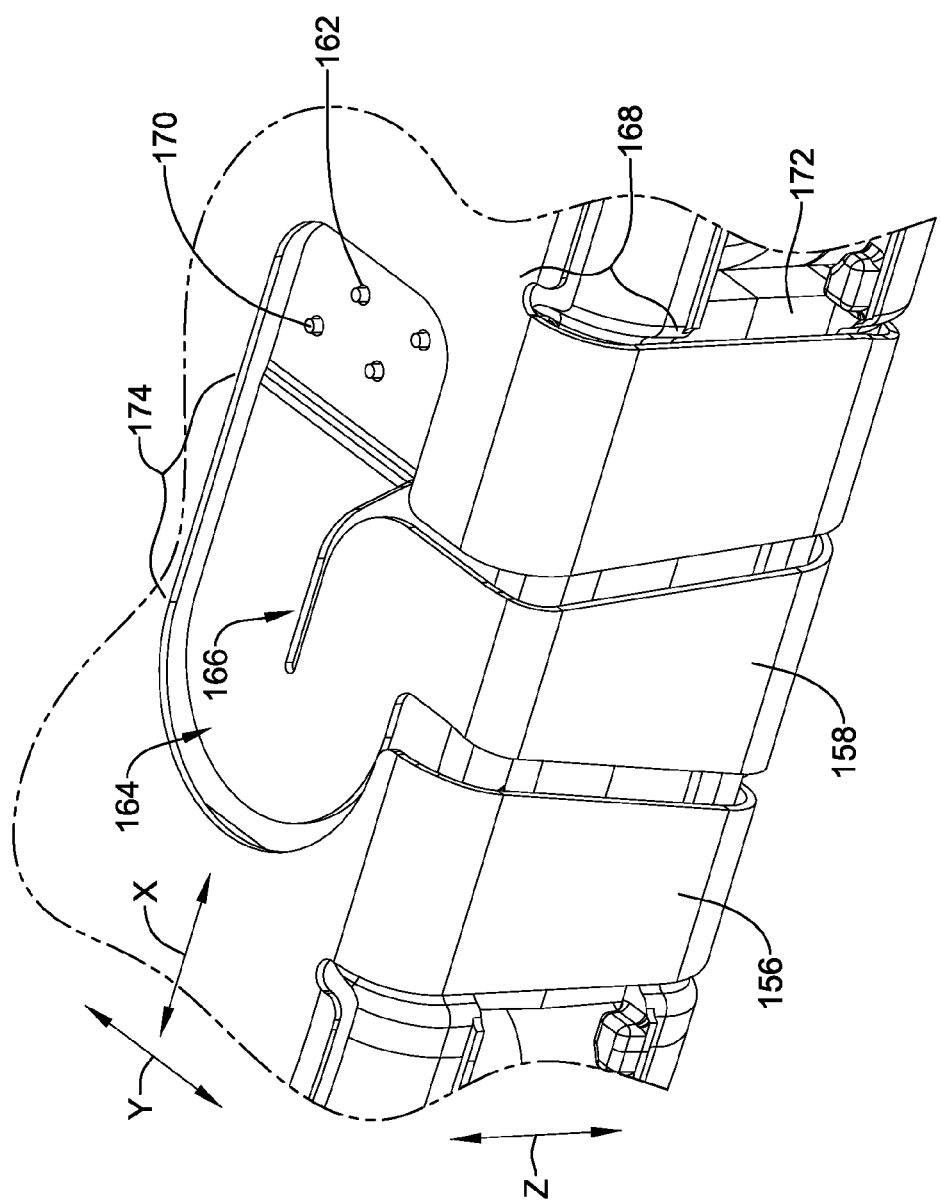

FIGS. 6A-6C show a first illustrative embodiment improving upon the example of FIGS. 5A-5C. Referring to FIG. 6A, the illustrative shield 150 includes leafs 152, 154 and junction arms 156 generally as in FIGS. 5A-5C, however, the connector 158 includes a strain relief structure shown at 160 designed to prevent stress/strain at the through holes 162.

The detail view in FIG. 6B shows that the leafs 152, 154 are connected with the junction arms 156, with connector 158 extending from a first region—which includes the leaf 154, to a second region which includes the strain relief structure 160 and the structures for coupling to a component of the medical device, in this case, to the circuit board via through holes 162. The strain relief structure includes a C-shaped region 164 defining a gap 166 therein. Other arced or angular forms may be used instead, for example, rather than a C, a more angular version could be squared off. A more complex structure such as an S-shape may be used instead.

In this example, a bending region 168 is highlighted as well. The bending region 168 is where the connector goes from a first plane to a second plane, as more clearly shown in FIG. 6C. In FIG. 6C, the bend region 168 is where the junction arms 156 and connector 158 wrap around the circuitry 172 and other components.

In one illustrative description of the example in FIG. 6C, the connector 158 wraps around the gap 166 after passing the bending region 168 and before reaching the connection location at holes 162. In this example, the bend occurs about an axis, X, and strain relief is provided in each of direction X as well as two orthogonal directions Y, Z thereto, such that each of X, Y and Z are mutually orthogonal. In another description of the example of FIG. 6A/B/C, the connector 160 includes a portion marked at 174 (FIG. 6C) that runs parallel to the axis of the bending region 168.

The portion of the connector 158 which passes around the gap 166 (that is, C-shaped region 164) is configured to disperse forces in at least two directions—here, X and Y. The gap 166 allows for strain relief in each of the X, Y and Z directions. For example, the portion of the connector 158 closer to the bending region 168 relative to the gap 166 can lift slightly in the Z direction if there is motion in the Z direction, removing strain both at the pins 170 and at the bending region 168, which would otherwise tend to pinch. The gap 166 itself allows movement in the X dimension. The C-shape surrounding the gap 166 allows greater flexibility in the Y direction as well, dispersing forces that would be caused by movement in the X-Y plane.

The shield 150 shown in FIGS. 6A-6C, including the connector 158, may be shaped using laser cutting, for example. The through holes may be formed during assembly of a flex circuit that serves as the shield 150, and may be formed by ordinary flex circuit methods or using the enhanced through-hole designs discussed in detail in U.S. Provisional Pat. App. No. 62/143,463, titled IMPLANTABLE MEDICAL DEVICES HAVING FLEXIBLE ELECTROMAGNETIC INTERFERENCE AND DUMP RESISTOR SHIELDS, the disclosure of which is incorporated herein by reference. Other manufacturing processes may also be used (stamp or die cut, for example) to produce a gap 166 providing the desired strain relief.

Some examples include two or three layer flex circuits, having two or three layers of conductive material separated by an insulator, with one or more layers of insulating material covering the conductive materials as well. One or more layers of the conductive material may also serve circuit functions. An illustrative example is further described in U.S. Provisional Pat. App. No. 62/143,463, titled IMPLANTABLE MEDICAL DEVICES HAVING FLEXIBLE ELECTROMAGNETIC INTERFERENCE AND DUMP RESISTOR SHIELDS, the disclosure of which is incorporated herein by reference. In an example described in the copending provisional application, the shield leafs 152, 154 include two conductive layers and one resistor layer, with dielectrics and adhesives therebetween, while the connector 158 omits certain layers, including one of the conductive layers, to achieve higher flexibility.

Figure 7A:
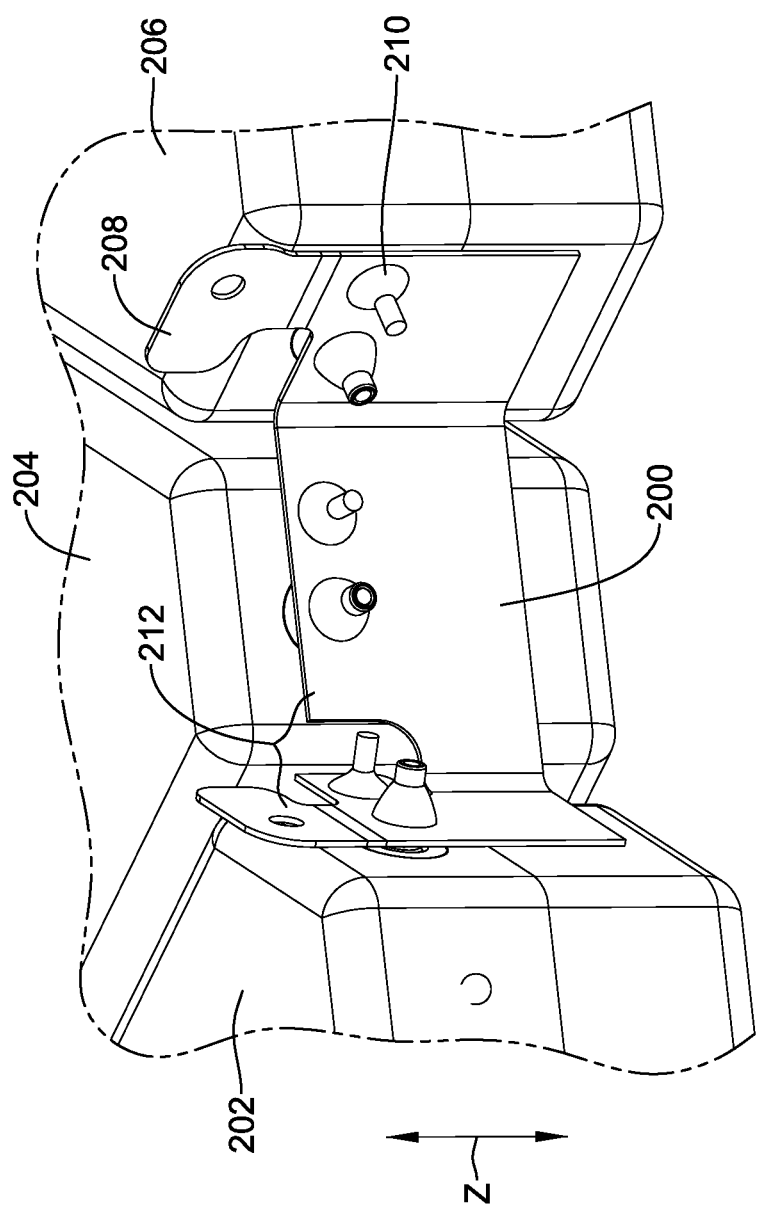
FIGS. 7A-7B show a battery flex circuit and highlight certain difficulties with attachment thereto.
Figure 7B:
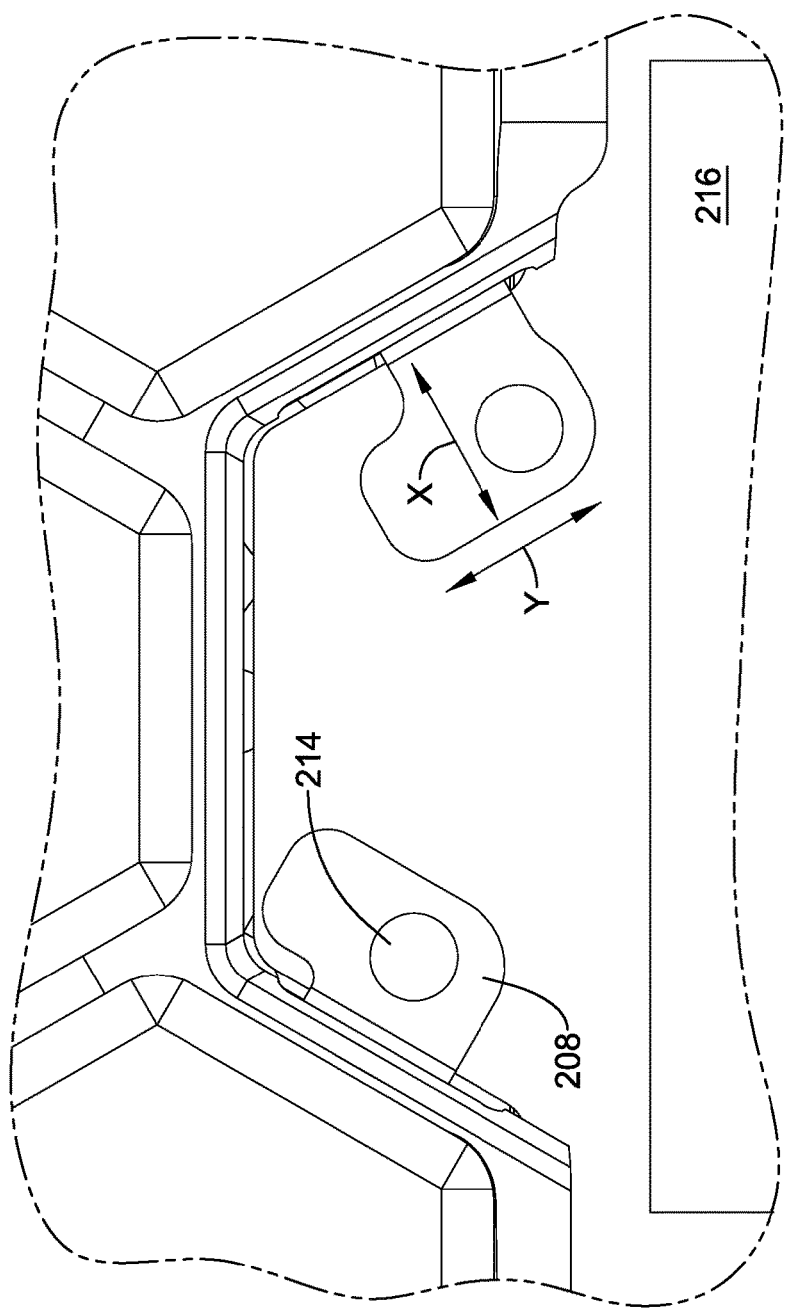

FIGS. 7A-7B show a battery flex circuit and highlight certain difficulties with attachment thereto. Referring to FIG. 7A, a flex circuit is shown at 200 connecting together three batteries 202, 204, 206, and includes tabs 208 for coupling the batteries 202, 204, 206 to other circuitry in the device. The batteries 202, 204, 206 connect to the flex circuit 200 with pins 210 placed in through holes and then soldered to the flex circuit 200. In an example batteries 202, 204, 206 are connected in series, though in other examples they could instead by connected in parallel. The flex circuit 200 thus serves as the interconnect between the batteries and other components of the implantable medical device.

A cutout is shown at 212 and allows some reduction in the amount of force needed to bend the flex circuit 200 between battery cells 202 and 204. However, the cutout 212 does not extend into the flex circuit 200 in a way to address strain in each dimension if the battery cells 202 and 204 shift under cyclic or static forces. As can be seen in FIG. 7A, movement in the Z direction is not accommodated by any strain relief in this design. Instead, tab 208 would translate movement in the Z direction directly to the circuit board it is connected to. In short, the cutout 212 provides strain relief to the bend in the flex circuit 200, but does not provide strain relief to the tabs and pins for the connection of the flex circuit.

FIG. 7B illustrates that the tab 208, in use, may be bent at approximately 90 degrees in order to connect to the hybrid 216. The hybrid 216 may be a high power hybrid for a defibrillator, for example, or, for other devices, may instead be the single or low power hybrid of a device. Again, without any strain relief on the tabs 208, movement in the X and Y directions is translated directly to the board interconnects 214 of the hybrid 216, placing strain either on the board interconnects 214, or at the location where the tabs 208 are bent. It may be noted in this example that the board interconnects 214 are achieved by soldering; other examples may use pins on the hybrid 216.

Figure 8A:
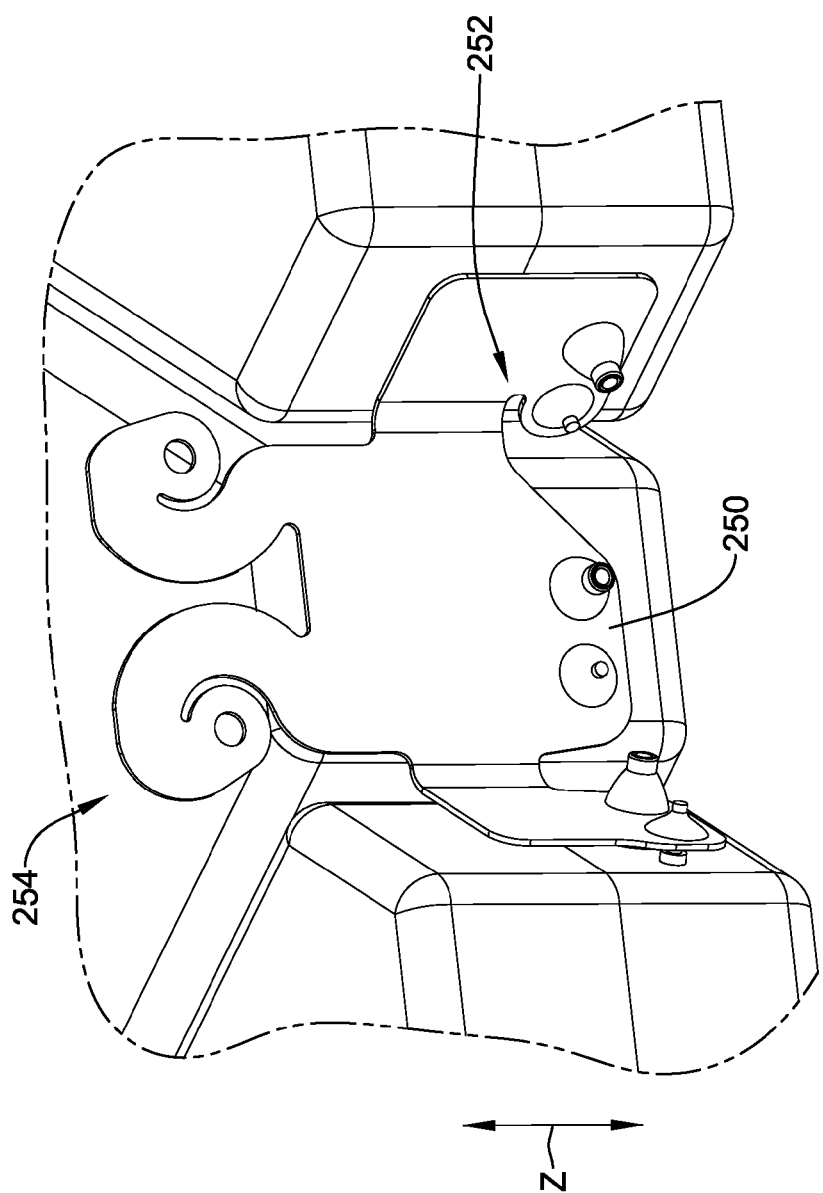
FIGS. 8A-8B show a second illustrative embodiment improving on the example of FIGS. 7A-7B.
Figure 8B:
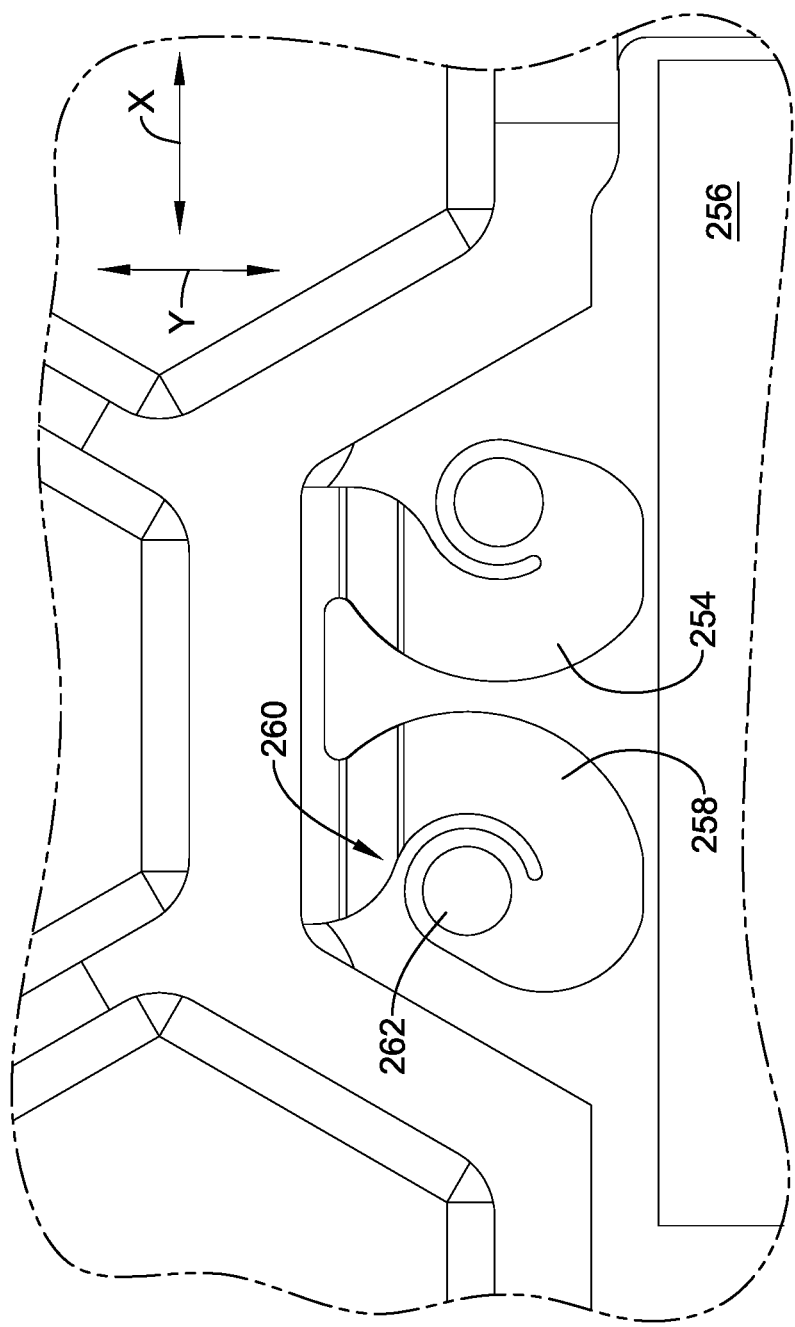

FIGS. 8A-8B show a second illustrative embodiment improving on the example of FIGS. 7A-7B. In this example, the battery flex 250 includes a number of further cutouts that do more to address strain relief. Cutout 252 provides greater strain relief by including a complex gap which extends in part around the battery pin. Strain relief structure 254 accommodates movement in several directions as well.

Referring to FIG. 8B, the details of strain relief structure 254 are highlighted relative to hybrid 256. The strain relief structure 254 includes a C-shaped portion 258 and a gap 260, with the gap 260 partially encircling the board interconnects 262 of the hybrid 256. The C-shaped portion 258 with gap 260 allows the strain relief to accommodate motion in dimensions X and Y highlighted in FIG. 8B. Motion in dimension Z (FIG. 8A) is also accommodated by allowing lifting off the hybrid 256 without excess pressure at the location where the tabs are bent or on the board interconnects 262.

The strain relief structure 254 can be formed using a flexible circuit which is laser cut in one example. Other manufacturing processes may also be used (stamp or die cut, for example) to produce a gap 260 providing the desired strain relief. In an example, single layer flex circuit (having one conductive layer and two insulation layers) may be used.

Figure 9:
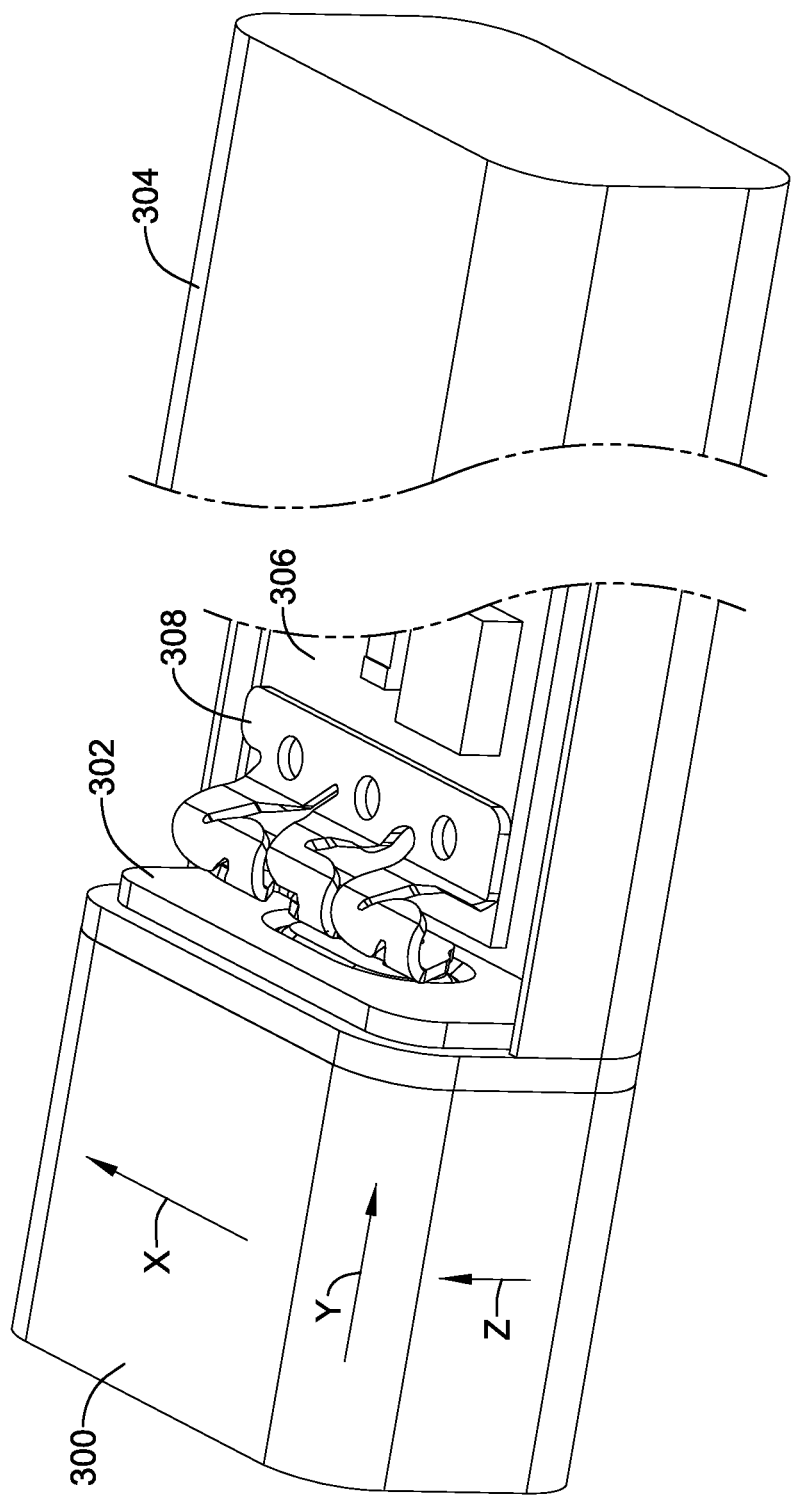
FIG. 9 shows a partly constructed implantable cardiac monitoring device incorporating a third embodiment.

FIG. 9 shows a partly constructed implantable cardiac monitoring device incorporating a third embodiment. The implantable monitoring device 300 includes a header 302 for attachment to electrodes and/or including an antenna component for communication purposes. A battery section is also shown at 304 on the opposite end of the device 300 from the header 302. In-between is the operational circuitry 306, which is provided on a hybrid/circuit board and is coupled by an interconnect 308 to the header. Another interconnect (not shown) also couples the operational circuitry 306 to the battery 304. In this example, the connection area for the operational circuitry 306 lies in a first plane, and the connection area for the header 302 lies in a second plane which is at an angle of more than 45 degrees relative to the first plane. In one embodiment, the connection area for the operational circuitry 306 is at an angle of about 90 degrees relative to the connection area for the header 302.

Figure 10:
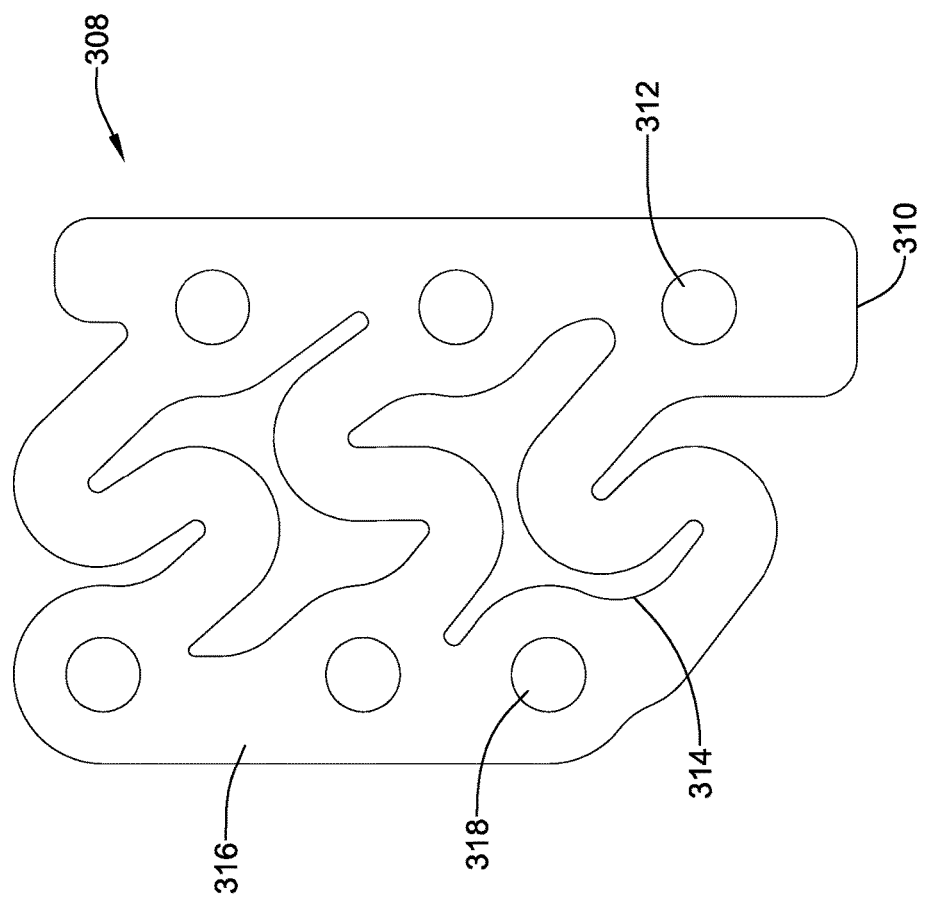
FIG. 10 is a detailed view of the third embodiment interconnection device from FIG. 9.

FIG. 10 is a detailed view of the third embodiment interconnection device from FIG. 9. The interconnect 308 includes a first connection area 310 having through hole 312 for connection to the hybrid (item 306 in FIG. 9), with a strain-relief flexible connection shown as a number of S-curves 314 that connects to a second connection area 316 having its own through holes 318 for connection to feed-through pins in the header 302 that in turn couple to electrodes and an antenna. The use of the S-curves 314 creates flexibility in all dimensions X, Y and Z (FIG. 9).

In one illustrative example, an S-curve 314 connects a radio transmitter line and component of the operational circuitry 306 to an antenna in the header 302. To support such functionality, the S-curve has an impedance matching circuit embedded therein in the form of one of a micro-strip, a stripline, a waveguide as illustrated below in FIG. 12, or other structures well known in the art of flex circuit design.

While the above discussion focuses on the use of flexible circuit designs incorporating strain relief structures for interconnection of the components in an implantable medical device, like designs may also find applicability in other fields such as non-implantable devices having medical or non-medical uses.

Figure 11A:
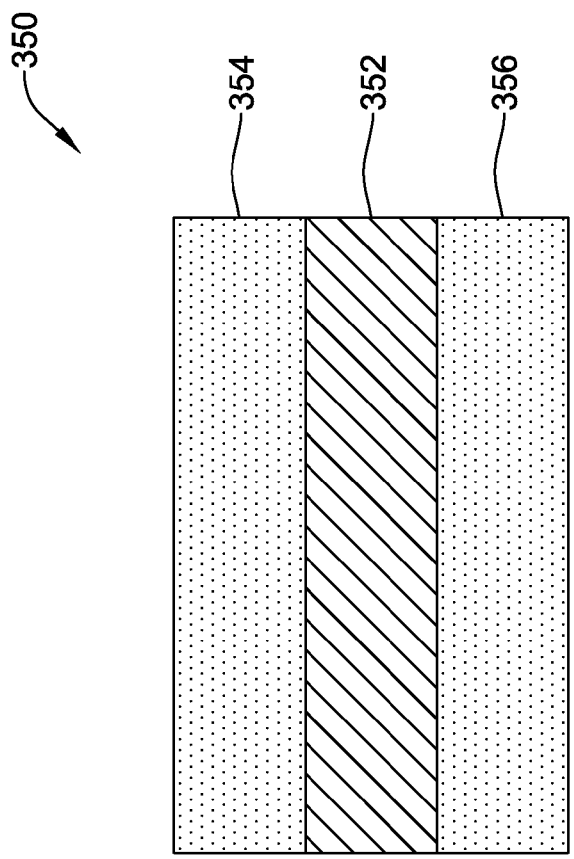
FIGS. 11A-11C show certain details of the construction of a flex circuit.
Figure 11B:
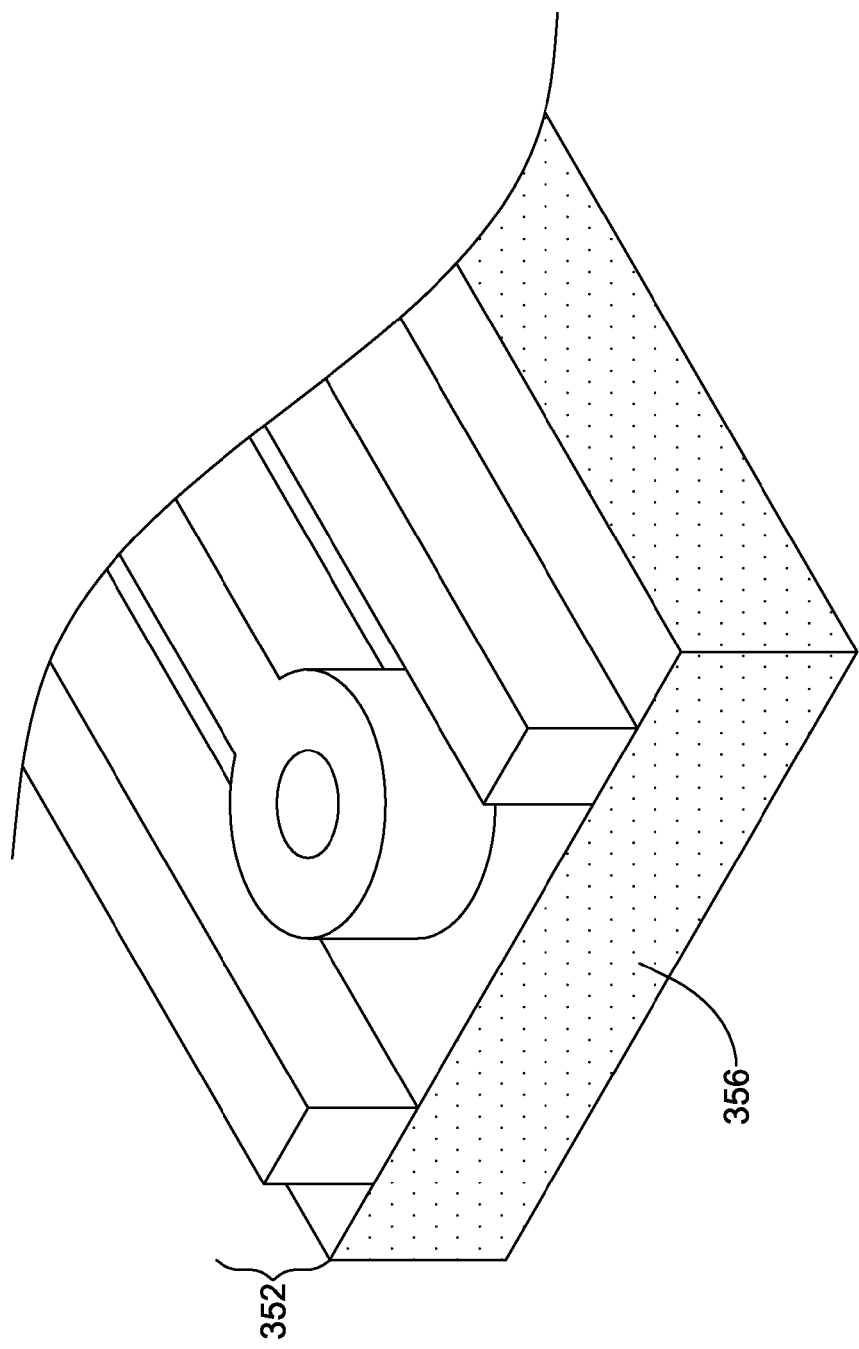
Figure 11C:
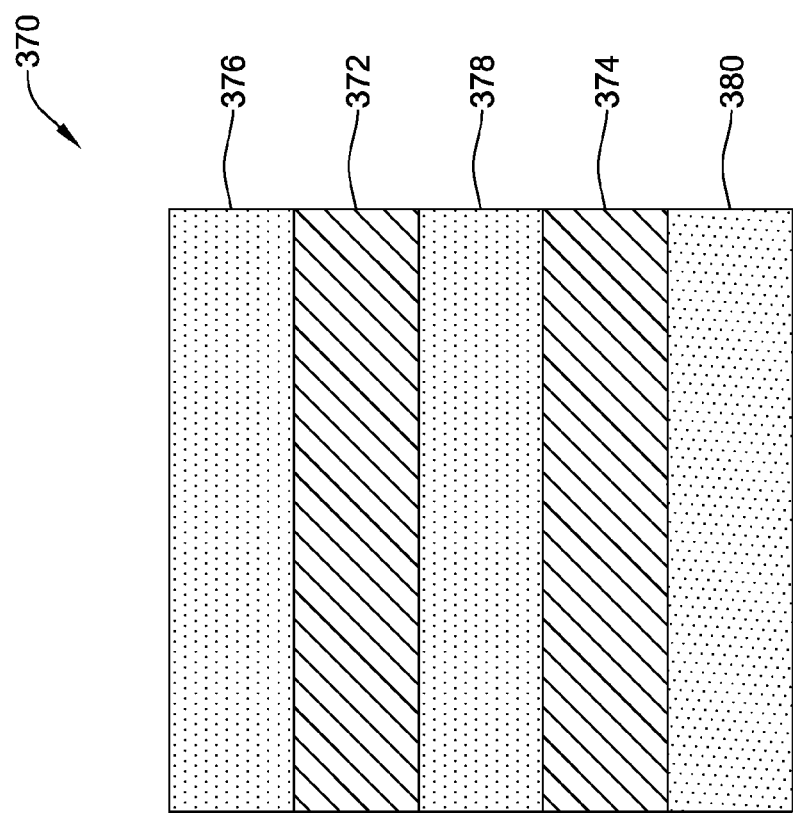

FIGS. 11A-11C show certain details of the construction of a flex circuit. Referring to FIG. 11A, a single layer flex circuit 350 includes a single conductive layer 352 sandwiched between two dielectric, insulating layers 354, 356. In addition to the layers shown, adhesive layers may be provided as well. FIG. 11B shows how the conductive layer 352 can be patterned and placed on top of an insulating layer 356 to provide the desired circuit functionality. Through holes may be pre-drilled or may be provided with laser ablation at desired locations, for example.

Common conductor materials include copper, nickel, gold, silver, tin, alloys of copper (such as phosphor bronze and beryllium copper), ferrous alloys, and nickel alloys (such as copper-nickel and nickel-chromium), as well as various other materials. Conductive layers can be electro-deposited or rolled and annealed, though other methods of forming the conductive layer may be used. Common insulating materials include polyimide, fluorinated ethylene propylene (FEP), and polyester films, though other materials may also be used. The multi-layer structure can be secured together using an adhesive such as an acrylic or epoxy. Patterns of conductors are typically formed by coating conductor foil with a photosensitive material and then using exposure and etching processes to remove the photosensitive material and conductor material not needed in the design, leaving behind the desired conductor pattern.

FIG. 11C shows a two layer structure. Here, the flex circuit 370 includes a first conductive layer 372 and a second conductive layer 374, with three insulating layers 376, 378, 380. With a two layer structure, it becomes easier to create shielding and/or to provide specific circuit features.

Figure 12:
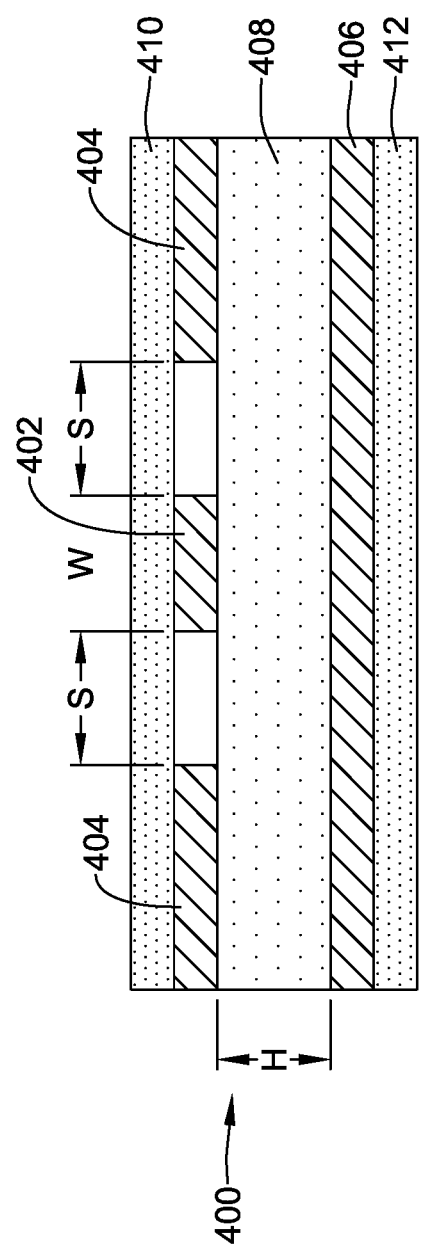
FIG. 12 shows how a flex circuit may be used to construct a transmission line.

When one of the connections in a flex circuit is intended as a transmission line, various designs can be used to aid in the electrical utility of the connection, including in particular the use of a micro-strip, in which a conductor is located above a single ground plane. In another example, a stripline can be created by placing a conductor between two ground planes. A further example is a grounded coplanar waveguide, which combines both concepts as shown in FIG. 12. The waveguide 400 includes a narrow strip 402 having a width W, surrounded by conductive material 404 at a distance S. A ground plane 406 is provided opposite a dielectric 408 having a thickness H. If the dielectric constant of the dielectric layer 408 is known, the characteristic impedance and effective dielectric of the waveguide can be calculated for the structure shown using well known formulas. This approach allows a line to be designed for communicating high frequency signals with impedance matching, as may be useful when one or more connections are to an antenna. Additional layers of dielectric 410 and 412 may be provided as well.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are The claimed invention is:

1. An implantable medical device (IMD) comprising:
   a first component having a first connection area;
   a second component having a second connection area;
   a connector for coupling to the first component and having a first region at a first end for coupling to the first connection area, and a second region at a second end for coupling to the second connection area, the connector comprising a flex circuit in at least the second region; wherein:
   the second region of the connector comprises a strain relief section to provide strain relief relative to at least one of the connection areas wherein the connector is manufactured by the use of laser cutting to create the strain relief section;
   the first connection area lies in a first plane; and
   the second connection area lies in a second plane different from the first plane.

2. The IMD of claim 1 wherein the connector extends from the first region to the second region around a bending location at which the connector bends from the first plane to the second plane.

3. The IMD of claim 1 wherein:
   the first plane defines X and Y dimensions in the first plane and a Z direction orthogonal to the first plane; and
   the strain relief section provides strain relief relative to motion in at least one of the X, Y and Z directions.

4. The IMD of claim 3 wherein the strain relief section comprises a C-shaped portion having an arc around a gap, the gap having a depth and a width, the depth being greater than the width and extending in the X direction.

5. The IMD of claim 1 wherein the connection area of the first component includes one or more pins, and the connector first region comprises one or more through holes for connection to the one or more pins.

6. The IMD of claim 5 wherein the strain relief section includes a gap that partly encircles at least one of the through holes.

7. The IMD of claim 1 wherein the first region also includes a strain relief section.

8. The IMD of claim 1 wherein the connector comprises at least one trace for coupling to the first component which includes an impedance matching microstrip.

9. The IMD of claim 1 wherein the connector comprises at least one trace for coupling to the first component which includes a coplanar waveguide.

10. The IMD of claim 1 wherein the first component is selected from the group consisting of a battery, a capacitor, or a hybrid carrying circuitry.

11. The IMD of claim 1 wherein the connector is one of a two-layer or a three layer flex circuit.

12. The IMD of claim 1 wherein the strain relief section includes an S-curve.

13. An implantable medical device (IMD) comprising:
    a first component having a connection area on a first plane;
    a connector comprising a flex circuit for coupling to the first component and having a first region at a first end and a second region at a second end, the first region for coupling to the connection area of the first component;
    wherein the connector comprises at least one strain relief section in at least one of the first region or the second region to provide strain relief relative to the connection area wherein the connector is manufactured by the use of laser cutting to create the strain relief section;
    wherein the second region of the connector lies in a second plane at an angle of at least 45 degrees relative to the second region in the first plane.

14. The IMD of claim 13 wherein the strain relief section includes a C-shaped portion.

15. The IMD of claim 13 wherein each of the first and second regions include a strain relief section.

* * * * *